United States Patent
Baaske et al.

(10) Patent No.: US 10,182,893 B2
(45) Date of Patent: Jan. 22, 2019

(54) DENTURE AND METHOD OF PRODUCING A DENTURE

(71) Applicant: Ivoclar Vivadent AG, Schaan (LI)

(72) Inventors: Thomas Baaske, Grabs (CH); Konrad Hagenbuch, Haag (CH); Christian Frei, Naturns (IT); Markus Heinz, Naturns (IT); Ronny Watzke, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 46 days.

(21) Appl. No.: 14/365,138

(22) PCT Filed: Dec. 17, 2013

(86) PCT No.: PCT/EP2013/076888
§ 371 (c)(1),
(2) Date: Jun. 13, 2014

(87) PCT Pub. No.: WO2014/095852
PCT Pub. Date: Jun. 26, 2014

(65) Prior Publication Data
US 2015/0216638 A1    Aug. 6, 2015

(30) Foreign Application Priority Data

Dec. 17, 2012  (EP) .................... 12197441

(51) Int. Cl.
| | |
|---|---|
| *A61C 13/06* | (2006.01) |
| *A61C 13/08* | (2006.01) |
| *A61C 19/05* | (2006.01) |
| *A61C 13/00* | (2006.01) |
| *A61C 13/01* | (2006.01) |

(Continued)

(52) U.S. Cl.
CPC ............ *A61C 13/081* (2013.01); *A61C 13/00* (2013.01); *A61C 13/0004* (2013.01); *A61C 13/0006* (2013.01); *A61C 13/01* (2013.01); *A61C 13/097* (2013.01); *A61C 13/1006* (2013.01); *A61C 13/1016* (2013.01); *A61C 19/045* (2013.01);

(Continued)

(58) Field of Classification Search
CPC ........................................ A61C 13/00–13/225
See application file for complete search history.

(56) References Cited

U.S. PATENT DOCUMENTS

| | | | |
|---|---|---|---|
| 3,094,778 A * | 6/1963 | Mailland ................ | A61C 13/00 433/177 |
| 4,443,197 A * | 4/1984 | Fusayama .............. | A61K 6/083 106/35 |

(Continued)

FOREIGN PATENT DOCUMENTS

WO    wo2012155161   * 11/2012

*Primary Examiner* — Yogesh Patel
(74) *Attorney, Agent, or Firm* — Ann M. Knab; Thad McMurray

(57) ABSTRACT

The invention relates to a denture, made of teeth, in particular prefabricated teeth, and of a denture base made of a gingival material, comprising cavities for teeth in which cavities for the teeth are mounted, in particular attached by bonding, characterized in that the denture base (12) is produced by a CAD/CAM process forming the cavities (20) for the teeth (14), and in that cervical areas (40a) of the teeth (14) extending through the basal surface (16, 18) of the denture base (12) are removed, in particular abraded or milled.

14 Claims, 4 Drawing Sheets

(51) Int. Cl.
   *A61C 19/045*   (2006.01)
   *A61C 13/36*   (2006.01)
   *A61C 13/097*   (2006.01)
   *A61C 13/093*   (2006.01)

(52) U.S. Cl.
   CPC ......... *A61C 19/05* (2013.01); *Y10T 29/49567* (2015.01)

(56) References Cited

U.S. PATENT DOCUMENTS

| | | | | |
|---|---|---|---|---|
| 4,470,815 | A * | 9/1984 | Hazar | A61C 13/00 264/18 |
| 4,583,947 | A * | 4/1986 | Hazar | A61C 13/00 264/18 |
| 9,820,833 | B2 * | 11/2017 | Noack | A61C 13/0022 |
| 2011/0236856 | A1 * | 9/2011 | Kanazawa | A61C 13/1003 433/199.1 |
| 2012/0276502 | A1 | 11/2012 | Marshall | |
| 2014/0087327 | A1 | 3/2014 | Noack | |
| 2015/0134094 | A1 | 5/2015 | Thompson et al. | |
| 2015/0216638 | A1 * | 8/2015 | Baaske | A61C 13/00 433/196 |

\* cited by examiner

DENTURE AND METHOD OF PRODUCING A DENTURE

CROSS-REFERENCE TO RELATED APPLICATIONS

This application is a National Stage application of International patent application PCT/EP2013/076888 filed on Dec. 17, 2013, which claims priority to European patent application No. 12197441.4 filed on Dec. 17, 2012, the disclosures of which are incorporated herein by reference in their entirety.

The invention relates to a denture, according to the preamble of claim 1, as well as to a method of producing a denture, according to the preamble of claim 12.

For a long time, namely for several decades, dentures have been produced as partial and/or full dentures such that artificial teeth which are to replace natural teeth are embedded in a material simulating the gingiva of the patient.

In order to at least reduce possible complaints by patients it is desired to optimize the position of the teeth also gnathologically. For this purpose, after reproducing the oral situation of the patient and placing a positive model into an articulator, the translational and rotational position of the respective tooth is reviewed and improved, if necessary, for instance by occlusal or incisal abrading of the tooth, before the teeth are set up in wax.

Numerous processes have become known to adjust and determine the position of the respective tooth relative to the denture base. For instance, it is insofar referred to DE 16 16 125. A further example of such processes from the 1980s is the solution according to U.S. Pat. No. 4,299,573.

In the following decades various processes have become known of how to implement the production of a denture using CAD/CAM and also to determine the position of the teeth accordingly.

As a basis for the production of a denture it has been known for some time to use a blank made of polymethyl methacrylate (PMMA), as is described, for instance, in DE20 2006 006 286 U1. In this solution a large blank is to be colored in flesh color for producing the denture base, and the denture for a jaw can be made from a single piece. The size of the respective blank is selected such that it is also possible to implement a full denture, i.e. with all teeth of a jaw.

This solution is especially advantageous for machine processing within a CAD/CAM process as such a blank is easy to machine in a milling machine. However, this solution requires to set up the teeth in wax accordingly upon completion of the denture base for an individual customization to the patient. This complicates the entire production process.

Accordingly, further attempts have been made to adapt the production process to machine realization. Thus, WO 2012/061652 A2 discloses a CAD/CAM process which is said to detect anatomical characteristics or markings of the patient digitally and to use them. These can, for instance, be certain spots on the upper jaw, the condylar axis or the like. However, it is difficult, and basically impossible based on current knowledge, to, for instance, refer to the occlusal plane based on this information alone, in order to insert the teeth in such a way that a gnathologically optimized masticatory movement is possible. Thus, in this process, too, a subsequent adaptation of the individual teeth must be undertaken so that it is practically not possible anymore to make the desired time savings at least when a satisfactory tooth result is desired.

Numerous further processes for optimizing CAD/CAM processes have been suggested for the production of dentures. Thus, in one suggested approach the denture base is to be configured as a two-part base, namely with a first, standardized part and a second part which is supposed to enable a flexible setting-up of the teeth. However, without corresponding efforts, in particular the optimized position of height of the teeth related to the respective antagonist and its neighboring teeth is not possible, either.

In contrast, the invention is based on the task of providing a denture according to the preamble of claim 1 and a method of producing a denture according to the preamble of claim 12 which makes possible to set up the teeth of a partial or full denture in an optimized manner in spite of computer-controlled machining.

This task is solved by claims 1 and 12. Advantageous developments may be taken from the subclaims.

According to the invention it is especially favorable that through the possibility to abrade or mill the prefabricated teeth in a basal manner, i.e. to machine the teeth in an appropriate manner, the position of height can be realized in a free manner. Consciously, slightly longer prefabricated teeth can be deployed which enable a better anchorage in the denture. The forces incurred in mastication include, besides vertical forces, above all horizontal forces. While the vertical forces can be absorbed relatively well due to the conical configuration of the cavities in the denture base, the horizontal forces exert a shear force on the connection between the denture base and the teeth, and this strains the adhesive joint. By correspondingly lengthening the tooth root in the denture base it is ensured that the load arm of the leverage effect of the horizontal masticatory forces is as long as possible.

By means of the optionally available use of a transfer template for setting up the teeth, the positions of the teeth to be set up in the respective cavities can be determined fast and precisely based on the target position targeted by the CAD software according to which the cavity is configured.

Thus, it is possible according to the invention to avoid manual intermediate processing of the teeth which renders the placement into the respective cavity problematic anyways.

While the denture base is typically made of a flesh-colored plastic material, acryl-based teeth or composite teeth can be used. These teeth can typically be machined by the same milling cutters as used for machining the basal side of the denture base without incurring increased tool wear.

However, according to the invention it is not foreclosed to use ceramic teeth, for instance teeth made of feldspar. These teeth can also be abraded basally in case of protrusion relative to the patient-specific jaw situation, where appropriate after changing the milling tool which can be done automatically in typical milling machines.

As an adhesive, any desired adhesives can be used, for example acrylic-based adhesives, two-component adhesives or heat-hardenable adhesives.

Alternatively, another type of fixture securing the tooth or teeth in the denture can also be used according to the invention. Thus the teeth may also be polymerized into the denture, snapped into place using a snap fastening, screwed into place similar to implants, clamped, or fixed mechanically or with chemical means in any other suitable way.

According to the invention, it is especially favorable that even in connection with limited space in the mouth of a patient a denture can be realized which is absolutely satisfactory in terms of aesthetics and dentistry.

In an advantageous embodiment occlusal or incisal dynamic interfering contacts can further be removed by abrasion or milling upon completion of the denture. For this purpose, it is especially favorable if a five-axis milling machine is used. Occlusal and incisal malocclusions are preferably abraded after the teeth have been glued in, i.e. before the basal side of the denture base is machined, or subsequent hereto.

According to the invention it is favorable if, for the realization of the inventive denture, impressions from the mouth of the patient are taken initially, for instance using an impression tray known per se. A set of standardized anterior teeth—or, where appropriate, molars—is attached to the impression tray and a registered bite position is realized in an appropriate manner. The position produced in this way which corresponds to the natural bite position of the teeth is now detected three-dimensionally in an appropriate manner, by corresponding scanning processes. The data on the position of height detected in this way serves—in combination with the known dimensions of the prefabricated teeth—to provide data for the design of the cavities in the denture base, for the determination of angular and height positions of the respective teeth.

In doing so, the gingival fit of the teeth is optimized to the upper maximum such that an anchorage of the tooth base in the cavity in the denture base to the best possible extent is possible.

According to the invention it is especially favorable if the teeth, after having been inserted into the denture base, i.e. the cavity thereat, are shortened to such an extent, where necessary, that the basal surface of the denture ends flush with the basal surface of the tooth. In this way, a patient-specific adaptation to the jaw situation is possible, without creating any irritations at the toothless portions of the jaw.

If necessary, the basal surface of the tooth can also be covered by a protective layer, for instance also an acrylic-based layer, wherein the protective layer may also be dyed in flesh colors or may be configured elastically, as required. The protective layer can have a relatively small thickness, for instance between 5 μm and 100 μm.

According to the invention it is favorable that the shear forces introduced into the tooth can be absorbed by the maximum vertical length of the cervical circumference of the tooth. Especially with limited space available, an ideal support of the prefabricated teeth can be realized in this way.

In a further modified embodiment it is also possible that milling is undertaken beyond the flush extension at those locations where a basal surface of the tooth extends through the basal surface of the denture and which thus needs to be abraded or milled. In this alternative the basal surface of the tooth is shortened slightly more, for instance by 500 μm, than what would be necessary for achieving a flush edging. The recess produced in this way will then be filled again with denture base material in order to produce a flush edging.

If there are interfering contacts in the occlusion position—as may be the case in relatively long prefabricated teeth—or interfering contacts which are produced by a simulated movement of the jaw joint, they are also removed preferably in the same milling machine—or manually, if appropriate—by an occlusal or incisal machining of the teeth.

Further advantages, details and features may be taken from the following description of several exemplary embodiments of the invention in conjunction with the drawings, in which.

Figure 1:
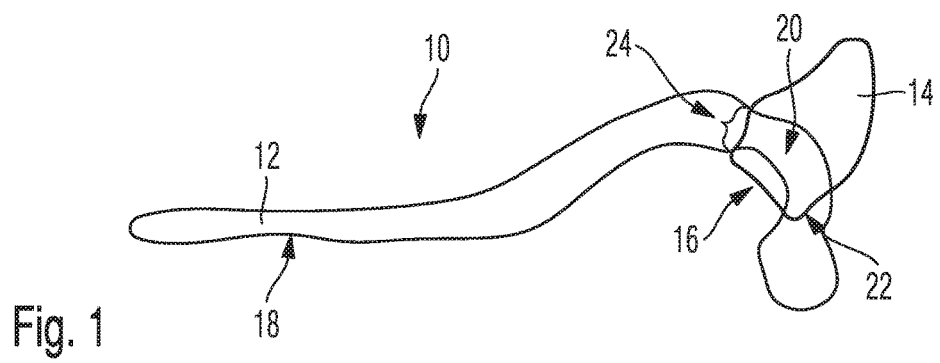
FIG. 1 shows a schematic view of the virtual section through an inventive denture, illustrating the denture base and the prefabricated tooth during penetration, yet not machined.

The denture 10 illustrated in FIG. 1 comprises a denture base 12 and a plurality of teeth, and one tooth 14 of the plurality of teeth is illustrated in FIG. 1, namely an anterior tooth.

As can be seen from FIG. 1, a basal surface 16 of the tooth 14 extends downwards beyond a basal surface 18 of the denture base 12. This is due to the fact that the position of height of the tooth 14 has to be adapted to the occlusal situation in the mouth of the patient. The protrusion of the basal surface 16 relative to the basal surface 18 would, however, lead to an anatomical incompatibility in the jaw of the patient. In order to prevent this from happening, so far the tooth 14 has been shortened considerably at its base such that the basal surface 18 comprising a wall thickness of, for instance, one millimeter extended beneath the basal surface 16.

When considering the provision of the respective cavity 20, it was assumed, before this invention, that in particular the vertical forces of the denture base beneath the basal surface 16 had to be absorbed, which meant forces in a normal disposition relative to the basal surface 16.

According to the invention it is provided, in contrast to this, that these forces are partially absorbed by the jaw of the patient which extends beneath the basal surface 18 from the V-shaped reception surface 22 of the denture base 12, viewed in the cross section. Forces which are indeed introduced vertically are absorbed and supported thereat easily, whereas it is to be understood that the tooth 14 around the cavity 20 is completely surrounded by the material of the denture base 12. In any case, the material thickness is sufficient to absorb the tensile forces which are introduced onto the denture base 12 at the location of the V-shaped reception surface 22.

According to the invention, the entire height of the side surfaces 24 is available for receiving and transferring shear forces. Especially in connection with molars, but also partially with anterior teeth, the mastication loop produces relatively large lateral forces which, due to the leverage at the peak of the respective tooth 14, propagate through the tooth 14 and then have to be supported and absorbed by the denture base 12.

According to the invention it is favorable that, especially in connection with restricted jaw situations, the entire height of the denture base 12 is available for supporting these shear forces such that the load arm produced by the principle of the lever is maximized which is relevant especially in connection with a relatively thin configuration of a denture base 12.

Figure 2:
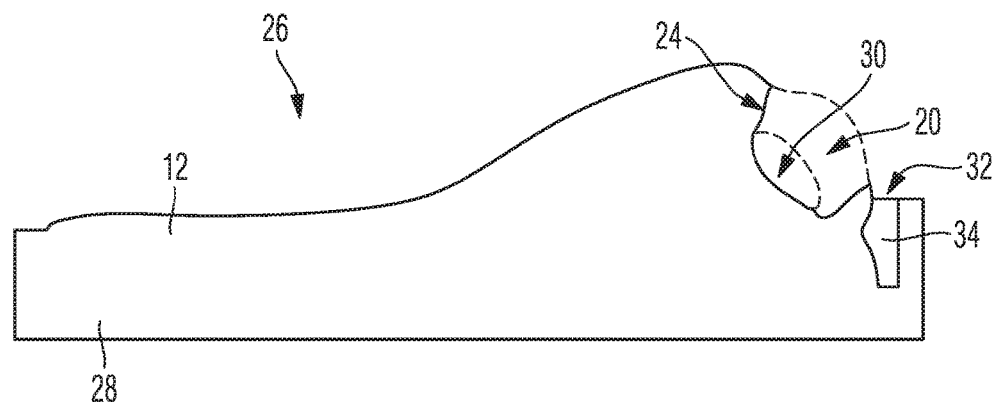
FIG. 2 shows the denture base according to FIG. 1 after the production of the cavity.

It is now obvious from FIG. 2 how the cavity 20 is inserted into the denture base 12 for receiving the tooth 14. Here, the removed regions of the denture base 12 are indicated by dotted lines. The machining is carried out from the upper side of the denture base 12, i.e. from the occlusal side.

As can be seen, the denture base 12 is initially configured similar to a disc 28, in a manner corresponding to DE 20 2006 006 286 U1. Machining is initially carried out completely from the upper side 26, and the cavity 20 is exactly machined in the area of the side surfaces 24 while the cavity base 30 is removed generously in order not to affect the reception of the tooth 14 in the cavity 20 according to FIG. 3.

Figure 3:
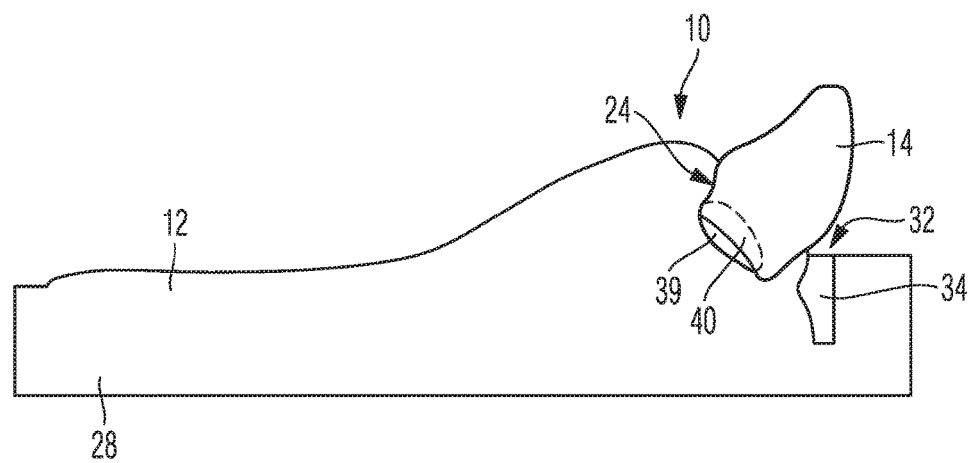
FIG. 3 shows the denture base according to FIG. 1 with the inserted prefabricated tooth.

As can be seen from the comparison of FIGS. 2 and 3, a generous excess reception space 39 is provided in which excess glue can be received. In the area of the cavity base 30, material removal is insofar provided to a larger extent than what would be required in connection with the conditions of the basal surface 16 of the tooth.

As can be seen, a recess 32 is configured on the side of/beneath the cavity 20 which is intended to further enable an easier removal of the subsequent denture 10 from the disc 28. However, a bar 34 remains which further connects the denture base 12 to the disc 28 until the end of the milling process.

It can be seen from FIG. 3 how the tooth 14 is inserted into the cavity 20. Before inserting the tooth, the side surfaces 24 are provided with a respective adhesive and/or the cervical exterior of the tooth 14.

Further machining is carried out after the adhesive has hardened, for instance with the aid of the supply of heat or with the help of the respective chemical reaction in connection with an adhesive glued on similar to an instant adhesive or a two-component adhesive.

As soon as the adhesive has hardened sufficiently, machining of the denture base 12 from the basal side is carried out. For this purpose, the basal side 18 of the denture base is initially milled as desired such that it is adapted to the anatomy of the jaw. This also includes the removal of basal areas of the tooth 14 such that the basal side 16b of the tooth 14 is anatomically shaped, and forms a considerable recess relative to the basal side 16 of the prefabricated tooth according to FIG. 1.

As can be seen, the side surfaces 24 of the cavity 20 are not affected by this machining process and secure the tooth, in particular in the area of the V-shaped reception surface 22.

Figure 4:
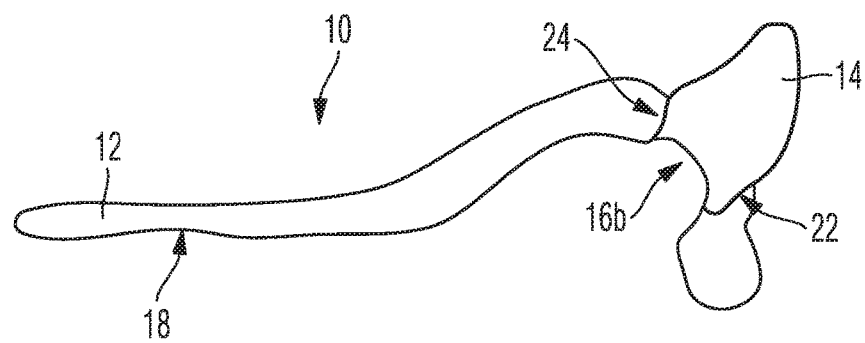
FIG. 4 shows the denture according to FIG. 1 after the inventive basal machining of the tooth.

As can be seen from FIG. 4, the bar 34 is detached in the last step such that the denture 10 is provided as a finished product, as illustrated in FIG. 4. FIGS. 5 to 8 illustrate a method corresponding to FIGS. 1 to 4, however, in connection with molars. Here, the same reference signs correspond to the same or respective parts.

Figure 5:
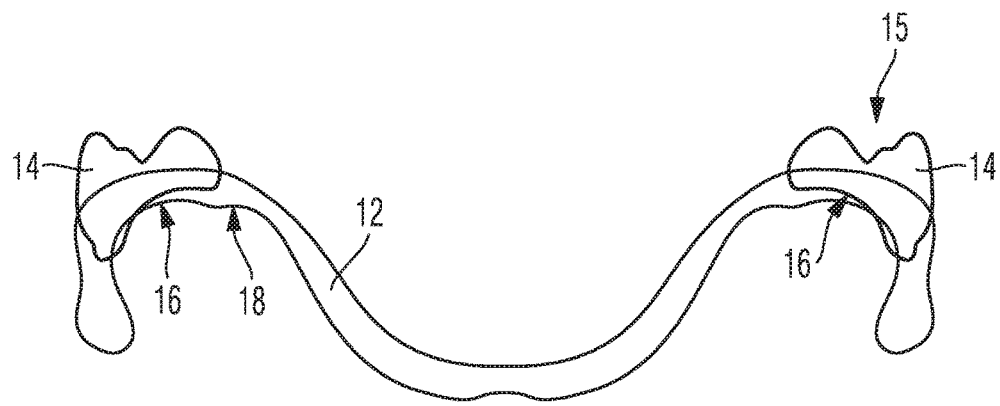
FIG. 5 shows an inventive denture in a modified embodiment illustrating the denture base and the virtual insertion of molars at the target positions in the denture base, according to FIG. 1.

As can be seen from FIG. 5, teeth 14, which are configured as molars here, have to be positioned at locations which extend through the denture base 12, i.e. which protrude from the bottom side of the denture base 12, which is the basal side thereat.

However, this protrusion is not provided in the entire area of the basal side 16 of the respective tooth 14 but only in a partial area of the basal side. This protruding area 40a of each molar 14 is now handled according to the invention.

Figure 6:
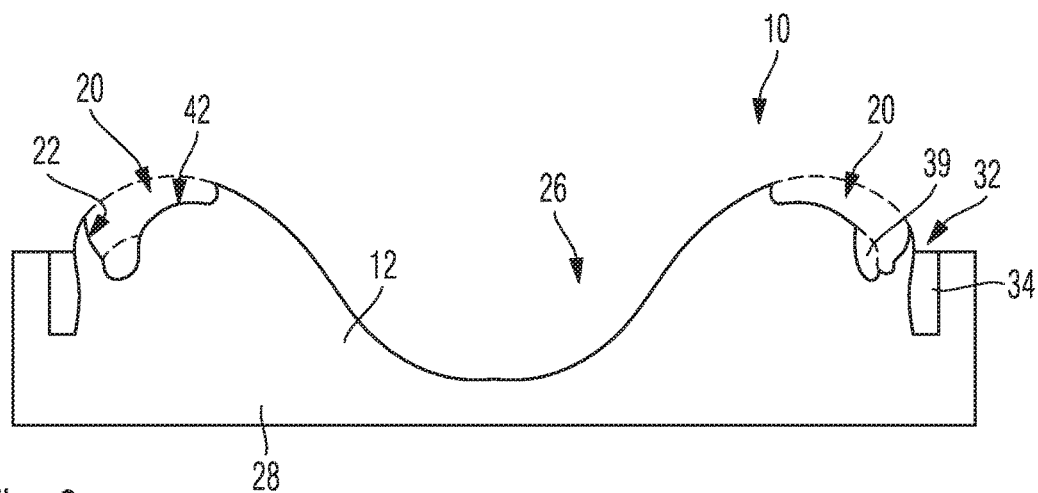
FIG. 6 shows the denture base according to FIG. 5 after the production of the cavities for the prefabricated molars.
Figure 7:
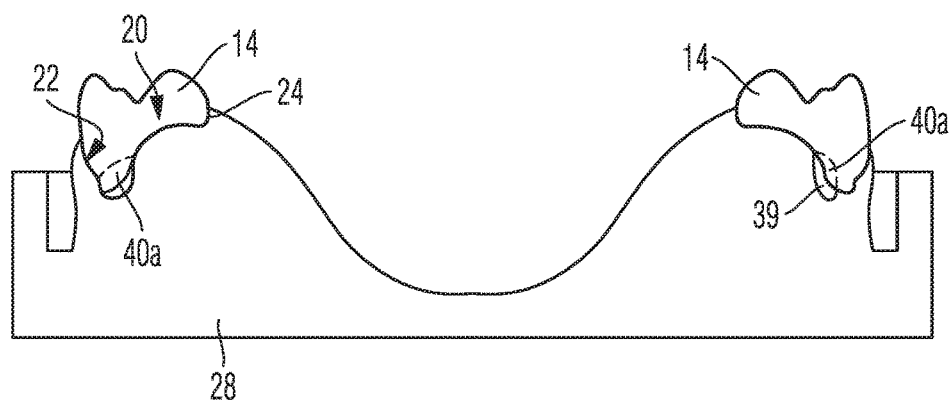
FIG. 7 shows the denture base according to FIG. 5 with inserted prefabricated molars.
Figure 8:
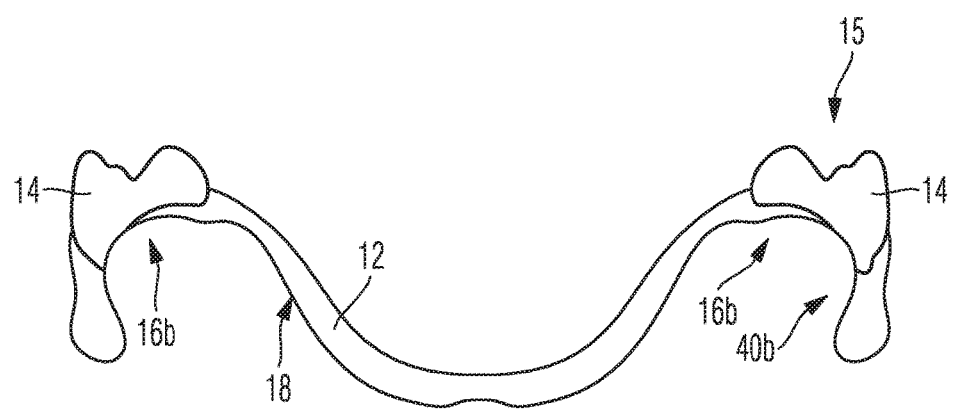
FIG. 8 shows the denture base according to FIG. 5 after basal machining of the molars at the denture base.

In FIG. 5 to FIG. 7 the finished condition at the upper side 26 of the denture 10 is illustrated; in the exemplary embodiments illustrated, the upper side 26 of the denture 10 is finished before the basal surface 18 of the denture is realized. In the semi-finished condition illustrated in FIGS. 2, 3, 5 and 7 the denture 10 is thus exceptionally stable and easy to machine.

As can be seen from FIG. 6, the masticating side 15 of the denture base 12 is initially milled in the desired manner. Cavities 20 for receiving molars 14 are produced. In the area of the protruding area 40a sufficient material is removed by milling in order to ensure that there is no contact between the prefabricated molar 14 and the milled denture base 12. By removing the protruding area 40a, an exposed area 40b is produced according to FIG. 7 which extends flush with the surrounding basal side 14 of the denture.

The denture base 12 offers a relatively large supporting area 42 for the respective molar 14, in a lateral disposition relative to the protruding area 40a. Together with the surface 22 which is inclined compared with the supporting area, the supporting area 42 offers a substantially V-shaped support holder which is interrupted by the area 40a.

As can be seen from FIG. 6, the prefabricated molar 14 can be inserted into the respective cavity 20 in an unimpeded manner. At this point in time the bottom side of the disc 28 is not machined and the molar 14 is glued into the cavity 20 in a way known per se, respectively, whereas the area 40a in turn remains free from adhesives.

The prefabricated molar 14 comprises a masticating surface 15 which—as described below—can be remachined, if necessary.

After the adhesive which extends across the entire supporting area 42 and the side areas 22 and 24 has hardened, machining of any occlusal interfering contacts of the molars 14 at the masticating surface 15 is carried out. It is to be understood that this machining process is only carried out on request and at those locations where it is considered necessary.

Subsequent to this, the bottom side of the disc 28 is inventively milled. In doing so, the basal side 18 of the denture base 12 is completely milled and the basal surface 16 of each protruding molar 14 in the area 40b is also machined such that a surface is produced which ends flush with the basal surface 18 of the denture. If necessary, in the area 40b—or even beyond this area—this surface will be provided with a protective layer which is elastic or consists of a denture base material. It is to be understood that, instead of the machining of occlusal interfering contacts described with reference to FIG. 6, machining can be carried out only now, for instance, when the finished denture is inserted into a milling machine and then malocclusions are determined.

Figure 9:
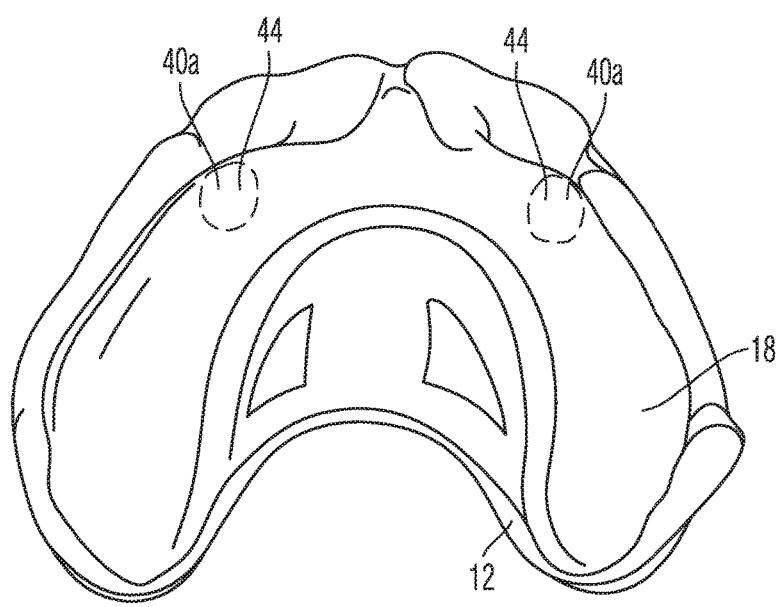
FIG. 9 shows a basal view of a denture illustrating the canine teeth protruding over the basal line.

It can be seen from FIG. 9 how basal protrusions or exposed areas 40b stand out from the basal side 18 of a denture base. In the exemplary case, one canine tooth 44 is affected each, whose prefabricated length is too large due to the oral situation of the patient. But still, an aesthetically fitting tooth is used which is associated with the remaining set of teeth and is shortened basally in a manner described in the aforementioned description, namely in one go during the machining of the basal side 18 of the denture base 12.

LIST OF REFERENCE SIGNS

10 denture(s)
12 denture base
14 tooth/teeth; molar(s)
15 masticating surface
16 basal surface
16b exposed basal surface 18 basal surface of the denture base
20 cavity/cavities
22 reception surface
24 side surfaces
26 upper side
28 disc
30 cavity base
32 recess
34 bar
40 area
40a protruding area
40b exposed area
42 supporting area
44 canine tooth

The invention claimed is:

1. A semi-finished denture comprising
prefabricated teeth, and
a denture base made of a gingival material,
wherein the denture base comprises cavities configured for receiving the the prefabricated teeth,
wherein the prefabricated teeth have cervical areas, and
wherein the prefabricated teeth are mounted in and attached to the cavities by adhesive bonding,
wherein one or more cervical areas of the prefabricated teeth extend through a basal surface of the denture base after the prefabricated teeth are adhesively bonded,
wherein the prefabricated teeth are mounted in and attached to the cavities by an adhesive in an unshortened manner regarding the masticating surface of the denture base.

2. The semi-finished denture according to claim 1,
wherein the teeth, after having been attached to the cavity of the denture base, are shortened, in such a manner that the basal surface of the denture ends flush with the basal surface of the tooth.

3. The semi-finished denture according to claim 1,
wherein at least one tooth of the denture is held in the associated cavity of the denture base exclusively in the cervical circumference, and
wherein the basal surface of the at least one tooth is exposed.

4. The denture according to claim 3,
wherein at least one tooth of the denture is held in by gluing, polymerizing, snapping or screwing the denture into the associated cavity.

5. The denture according to claim 1,
wherein the position of height of each tooth is determined by a position calculated by the CAD/CAM software, with regard to the chewing surfaces of molars and premolars or the cutting edges of anterior teeth, and
wherein a prefabricated tooth extends through the denture, predefined by the position of height.

6. The denture according to claim 1,
wherein each tooth is positioned spatially at the position calculated by the CAD/CAM software and
wherein the cavities for the teeth are each produced in a manner fitting the teeth in the denture base.

7. The denture according to claim 1,
wherein an exposed cervical area of a denture tooth is surrounded by the basal surface of the denture at the basal surface of the denture tooth and is machined, and
wherein the exposed area produced extends flush with the basal surface of the denture.

8. The denture according to claim 7,
wherein machined comprises milling or abrading.

9. The denture according to claim 1,
wherein at least one tooth extends through the denture at least partially and is abraded or milled in the area of penetration according to the layout of the basal surface of the denture.

10. The denture according to claim 1,
wherein the cavities for receiving the teeth are formed without undercuts from the masticating side of the denture base, by CAD/CAM milling.

11. The denture according to claim 1,
wherein the basal surfaces of the teeth are provided with a coating, at least partially on exposed areas, which coating extends at least partially from the basal surface of the tooth to the surrounding basal surface of the denture.

12. The denture according to claim 11,
wherein the coating comprises varnish.

13. The denture according to claim 1,
wherein at least one cavity for receiving a tooth comprises an excess receiving space at the cavity base in which excess glue in the adhesive gap between cavity and tooth is receivable.

14. The denture according to claim 1,
wherein the teeth comprise prefabricated teeth and wherein the cervical areas of the teeth are removed by abrading or milling.

* * * * *